United States Patent
Knoepfle et al.

(10) Patent No.: US 8,992,582 B1
(45) Date of Patent: Mar. 31, 2015

(54) FIXATION DEVICES AND METHOD

(71) Applicant: Stryker Leibinger GmbH & Co. KG, Freiburg (DE)

(72) Inventors: Christian Knoepfle, Donaueschingen (DE); Manfred Schmuck, Muehlheim-Stetten/Donau (DE); Karl Greiner, Muehlheim (DE); Markus Kuhn, Freiburg (DE)

(73) Assignee: Stryker Leibinger GmbH & Co. KG (DE)

( * ) Notice: Subject to any disclaimer, the term of this patent is extended or adjusted under 35 U.S.C. 154(b) by 33 days.

(21) Appl. No.: 13/975,588

(22) Filed: Aug. 26, 2013

(51) Int. Cl.
*A61B 17/88* (2006.01)
*A61B 17/80* (2006.01)

(52) U.S. Cl.
CPC .................................. *A61B 17/8071* (2013.01)
USPC ......................................................... 606/281

(58) Field of Classification Search
USPC ................................................. 606/281, 904
See application file for complete search history.

(56) References Cited

U.S. PATENT DOCUMENTS

| | | | |
|---|---|---|---|
| 1,638,006 A | 8/1927 | Aderer | |
| 2,481,177 A | 9/1949 | Tofflemire | |
| 2,502,902 A | 4/1950 | Tofflemire | |
| 3,474,779 A | 10/1969 | Wall | |
| 3,747,779 A | 7/1973 | Gross | |
| 4,230,104 A | 10/1980 | Richter | |
| 4,639,219 A | 1/1987 | Gagin | |
| 4,764,112 A | 8/1988 | Bergersen | |
| 4,797,095 A | 1/1989 | Armstrong et al. | |
| 4,904,188 A | 2/1990 | Baurmash | |
| 5,087,202 A | 2/1992 | Krenkel | |
| 5,839,899 A | 11/1998 | Robinson | |
| 5,842,856 A | 12/1998 | Casey | |
| 6,053,919 A | 4/2000 | Talos et al. | |
| 6,086,365 A | 7/2000 | Fields | |
| 6,227,861 B1 | 5/2001 | Cartledge et al. | |
| 6,257,884 B1 | 7/2001 | Chang | |
| 6,595,774 B1 | 7/2003 | Risse | |
| 6,827,574 B2 | 12/2004 | Payton | |
| 6,896,514 B2 | 5/2005 | DeVincenzo | |
| 7,322,987 B2 | 1/2008 | Schendel | |
| 7,351,058 B2 | 4/2008 | Fore et al. | |
| 8,118,850 B2 | 2/2012 | Marcus | |
| 8,282,635 B1 | 10/2012 | Amato | |
| 2001/0018176 A1 | 8/2001 | Branemark | |
| 2002/0013586 A1 | 1/2002 | Justis et al. | |

(Continued)

FOREIGN PATENT DOCUMENTS

DE 29615779 U1 1/1997
DE 19826860 A1 4/1999

(Continued)

*Primary Examiner* — Sameh Boles
(74) *Attorney, Agent, or Firm* — Lerner, David, Littenberg, Krumholz & Mentlik, LLP

(57) ABSTRACT

A plate system for bone fixation including intermaxillary fixation which has at least one plate with one opening and at least one bone screw for securing the plate to an adjacent bone and/or other anatomical structures (e.g., the gingival) with space maintained in between. The plate system provides a fixed connection at both the plate and the bone. A method for achieving fixation while maintaining space between the plate and bone includes placement of a spacer over the desired bone screw insertion point, followed by placement of the plate over the spacer so that the bone screw may be inserted through the plate while the spacer is held in position.

15 Claims, 4 Drawing Sheets

(56) References Cited

U.S. PATENT DOCUMENTS

| | | |
|---|---|---|
| 2002/0143336 A1 | 10/2002 | Hearn |
| 2002/0150856 A1 | 10/2002 | Payton |
| 2003/0160552 A1 | 8/2003 | Bacho et al. |
| 2004/0086824 A1 | 5/2004 | Kesling |
| 2004/0152046 A1 | 8/2004 | Minoretti et al. |
| 2005/0059971 A1 | 3/2005 | Michelson |
| 2005/0261690 A1 | 11/2005 | Binder et al. |
| 2005/0282115 A1 | 12/2005 | Gedebou |
| 2006/0069389 A1 | 3/2006 | Knopfle |
| 2006/0078849 A1 | 4/2006 | Parks |
| 2007/0162014 A1 * | 7/2007 | Campbell et al. ............... 606/69 |
| 2007/0254259 A1 | 11/2007 | DeVincenzo et al. |
| 2007/0259306 A1 | 11/2007 | Raines et al. |
| 2009/0036889 A1 | 2/2009 | Callender |
| 2009/0170050 A1 | 7/2009 | Marcus |
| 2011/0152946 A1 | 6/2011 | Frigg et al. |
| 2011/0152951 A1 | 6/2011 | Baker |
| 2012/0214120 A1 | 8/2012 | Marcus |

FOREIGN PATENT DOCUMENTS

| | | |
|---|---|---|
| DE | 19859503 A1 | 7/2000 |
| EP | 1385435 A1 | 2/2004 |
| EP | 1468656 A1 | 10/2004 |
| FR | 2760631 A1 | 9/1998 |
| GB | 1231425 A | 5/1971 |
| WO | 9727815 A1 | 8/1997 |
| WO | 9915115 A1 | 4/1999 |
| WO | 2007095577 A2 | 8/2007 |
| WO | 2010025263 A1 | 3/2010 |
| WO | 2011063368 A1 | 5/2011 |

* cited by examiner

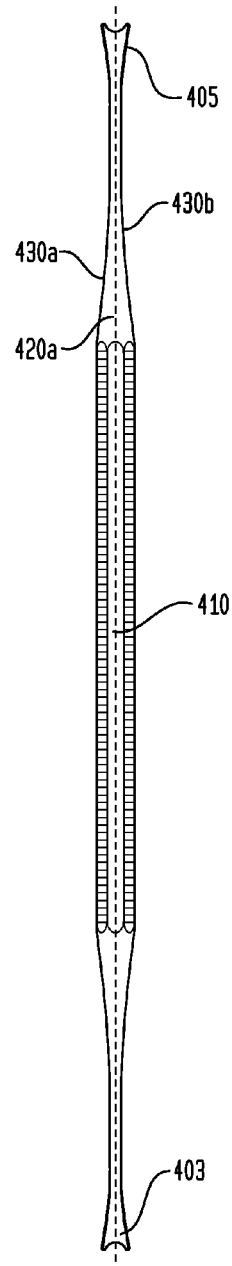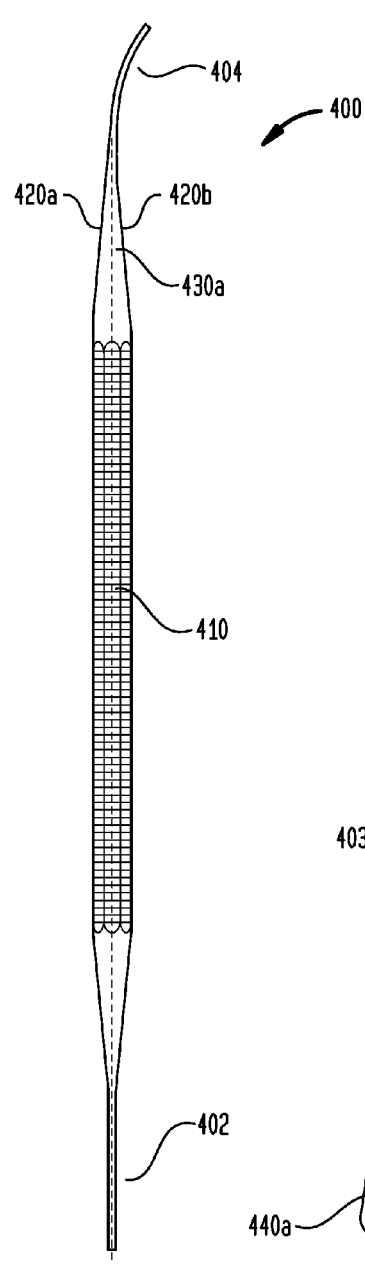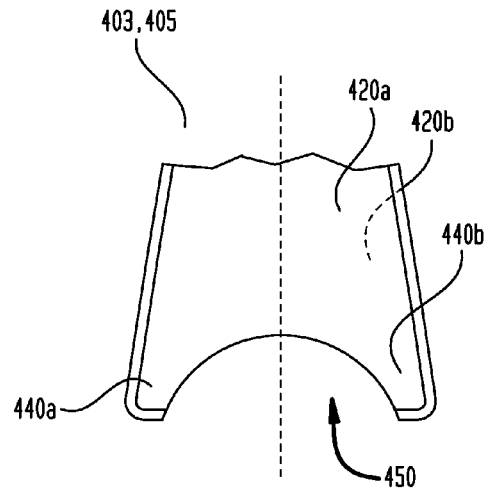

FIXATION DEVICES AND METHOD

BACKGROUND OF THE INVENTION

The fixation of the maxillary and mandibular jaw, also known as the upper and lower dental occlusal arches, is known as intermaxillary fixation or stabilization ("IMF"). IMF is a method used to repair maxillary and mandibular fractures by bringing bone fragments into proper position and alignment. These methods are also applied to the stabilization of single bone fragments.

Wiring techniques represent the earliest methods of securing the maxillary and mandibular jaw. The method involves utilizing metallic wires that are placed around one or more teeth at their base and then twisted using various methods to secure the teeth. The wires can be used in pairs or in greater multiples along the span of the dental arch forming a series, or, alternatively, a single strand of wire may incorporate a plurality of teeth. The methods of placing and twisting the wire so described achieve a secured fixation. The ultimate combination of the aforementioned methods involves the upper and lower arches secured along their respective lengths, and subsequently the maxillary and mandible jaws secured to one another with ligatures, thus accomplishing IMF. Unfortunately, the technique is tedious and time consuming. The wires can also interfere with dental hygiene.

Another conventional technique known to those of skill in the art includes utilizing arch bars in combination with wiring. Specifically, a metal, or sometimes plastic, bar is shaped to approximate the curvature of the maxilla or mandible. Ligatures are wrapped around the teeth and over the bar, and then twisted onto the bar. In a typical embodiment, arch bars have a plurality of hooks or tabs facing in the same direction. If two arch bars are used, the hooks or tabs of each one are placed in opposing directions so that ligatures may securely affix the jaws together. The semi-rigid arch bars span the dental arch providing stability along the upper end of the maxillary or mandible jaw even when a fracture or fractures exist between teeth, while the plurality of hooks allows placement of ligatures between the jaws at varying angles and lengths to allow various combinations of beneficial tension vectors.

Unfortunately, arch bars require significant time to secure in place and tend to interfere with dental hygiene. Another limitation of arch bars is that they may not provide satisfactory fixation in a fully or partially edentulous patient. Furthermore, the wire ligatures themselves are painful and frequently must be adjusted by the treating physician or other medical professional. Finally, removal of the arch bars may be difficult and carries with it the increased risk of dental injury and the need for operative anesthesia.

Another technique known to those of skill in the art involves placing a plurality of screws in the mandible or maxillary jaw between the tooth roots so as to avoid them. The screw head functions to allow ligatures to be wrapped around it and screw heads used may contain holes running continuously through their length enabling the passage of ligatures through the screw heads. Thus, ligatures may be secured to contiguous sets of screws in varying combinations to provide IMF. This technique is limited by an absence of overall structural stability which may be necessary in some instances, e.g., when a patient has fractures around the teeth.

Improving on the technique of placing screws into the bone, another method of securing arch bars involves using the same arch bar method described above, but substituting ligatures with a plurality of arms and attachment loops attached transverse to the longitudinal axis of the arch bar along its length, and placing screws into the bone through openings in the arms or attachment loops. This procedure and the apparatus associated therewith is disclosed in U.S. Pat. No. 8,118,850 ("the '850 patent") and U.S. Pat. Pub. No. 2011/0152951, the disclosures of which are hereby incorporated by reference herein. Such methods benefit from not having wires interfere with dental hygiene while simultaneously providing a secure connection. However, application of the method results in the arch bar pressing against the gingiva when in use, rendering the gingiva vulnerable to pressure necrosis.

There exists a need for a method utilizing an anchor plate or dental arch bar in an IMF procedure without causing pressure necrosis.

BRIEF SUMMARY OF THE INVENTION

One aspect of the present invention may be a method of fixation comprising the steps of placing a portion of a spacer adjacent to a first bone at a first location, placing a first plate so that the portion of the spacer may be located between the first plate and the first bone, inserting a first bone screw through the first plate at the first location while the portion of the spacer remains between the first plate and the first bone, and removing the portion of the spacer from between the first plate and the first bone so that the first plate remains spaced apart from the first bone.

In some embodiments, the first bone may be a maxilla and the method may further include the step of bending the first plate to approximate the shape of the maxilla.

In some embodiments, the first bone may be a mandible and the method may further include the step of bending the first plate to approximate the shape of the mandible.

In some embodiments, the portion of the spacer placed adjacent to the first bone at the first location may include tines having tapered distal ends. In some such embodiments, the first bone screw may be inserted through the tines. In further embodiments, the first bone screw may be inserted through a first attachment loop of the first plate. In still further embodiments, the first attachment loop may be bent with respect to the remainder of the first plate.

In some embodiments, a portion of the spacer may be placed adjacent to the first bone at a second location and a second bone screw may be inserted through the first plate at the second location while the portion of the spacer remains between the first plate and the first bone. In some such embodiments, the portion of the spacer placed adjacent to the first bone at the second location may include tines having tapered distal ends. In further embodiments, the second bone screw may be inserted through the tines. In still further embodiments, the second bone screw may be inserted through a second attachment loop of the first plate. And in still further embodiments, the second attachment loop may be bent with respect to the remainder of the first plate.

In some embodiments, the step of inserting the first bone screw may include fixing a portion of the first bone screw to the first plate. In some such embodiments, the first bone screw may include a first bone screw head formed of a hard material and the first plate may include a portion formed of a soft material and insertion of the first bone screw may result in the first bone screw head deforming the portion of the first plate.

In some embodiments, the first bone may be a maxilla and the method may further comprise the steps of placing a portion of the spacer adjacent to a second bone at a second location, the second bone being the mandible, placing a second plate so that the portion of the spacer may be located between the second plate and the second bone, inserting a second bone screw through the second plate at the second location while the portion of the spacer remains between the second plate and the second bone, and removing the portion of the spacer from between the second plate and the second bone so that the second plate remains spaced apart from the second bone.

In another aspect, the present invention may comprise a plate system comprising of a first bone screw further comprising a countersunk preformed thread and therebelow a self-tapping screw shank, wherein the countersunk preformed thread of the first bone screw may be fixed to a first plate of semi-rigid material comprising a countersunk opening wherein the countersunk preformed thread may be located in the opening such that the cavities of the preformed thread are filled with plate material, wherein the self-tapping screw shank of the first bone screw may be embedded and fixed in a bone to a certain depth, and wherein a space may exist between the plate and the adjacent bone.

In some embodiments, the connection between the plate and the bone screw may be supported by friction such that the bone screw does not back out of the plate when subject to forces.

In some embodiments, the plate may comprise a first attachment loop, connected to the remainder of the plate as a single material and oriented transverse to the plate length. In some such embodiments, the first attachment loop may be bent relative to the remainder of the plate. In further embodiments, the plate may further comprise a second attachment loop, connected to the remainder of the plate as a single material and oriented transverse to the plate length.

In some embodiments, the bone screw may comprise a button head and cross-recess screw drive.

In some embodiments, the screw shank may be self-drilling.

In some embodiments, the first bone screw may be embedded and fixed in a maxilla. In some such embodiments, a second bone screw may be inserted through a second plate system and embedded and fixed in a mandible.

BRIEF DESCRIPTION OF THE DRAWINGS

A more complete appreciation of the subject matter of the present invention and the various advantages thereof can be realized by reference to the following detailed description, in which reference is made to the accompanying drawings:

FIG. 4A is a top view of a spacer for use in placing the plates and screws of FIG. 1.

FIG. 4B is a side view of the spacer of FIG. 4A.

FIG. 4C is a partial top view of the spacer of FIG. 4A.

DETAILED DESCRIPTION

Figure 1:
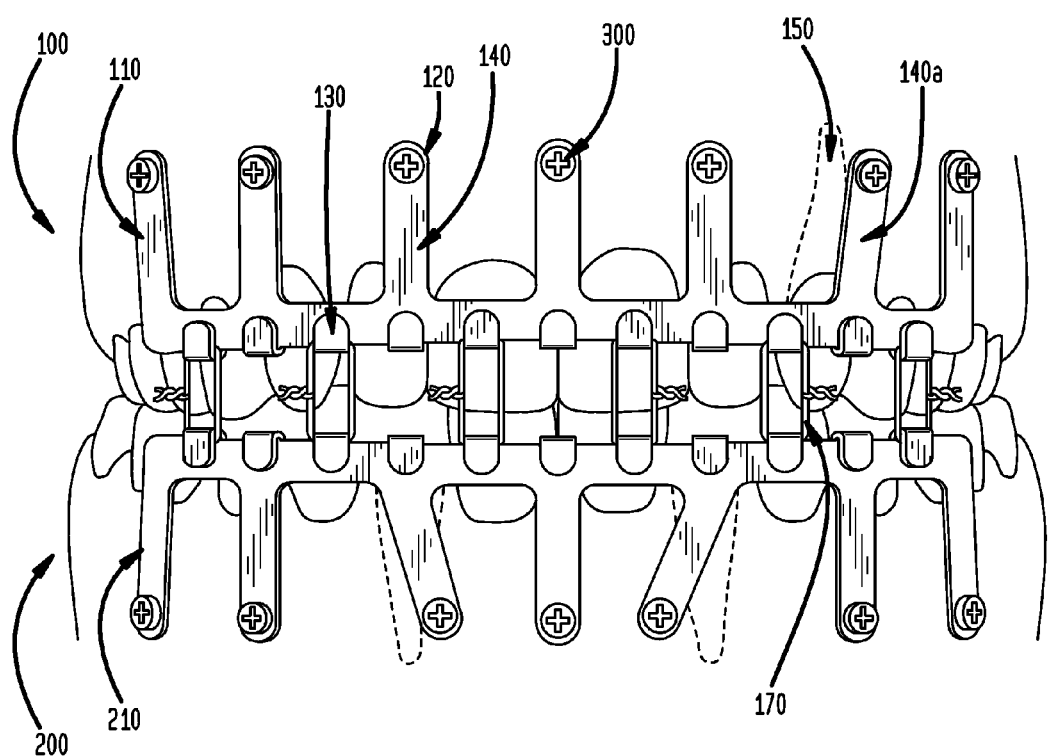
FIG. 1 is a perspective view of a full dental arch having first and second plates and a plurality of screws in place across the dentition, according to one embodiment.
Figure 2A:
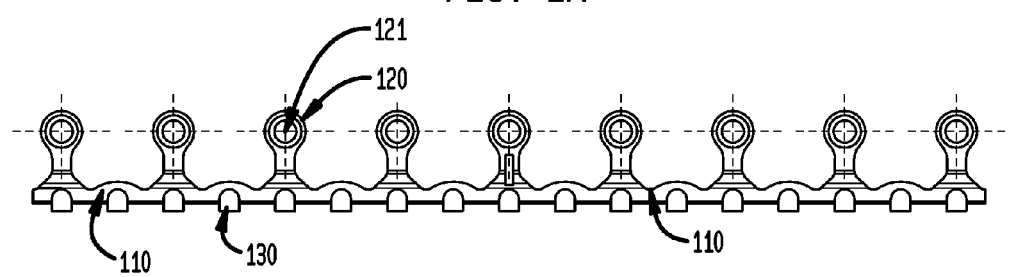
FIG. 2A is a frontal view of the first plate shown in FIG. 1 prior to bending to approximate the shape of a mandible or maxilla.
Figure 2B:
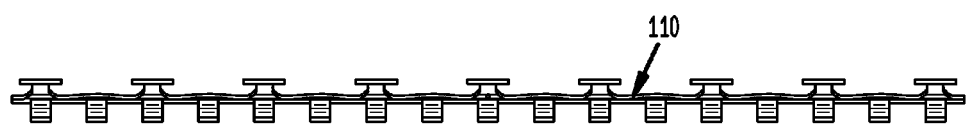
FIG. 2B is a top view of the first plate shown in FIG. 1 prior to bending to approximate the shape of the mandible or maxilla.
Figure 2C:
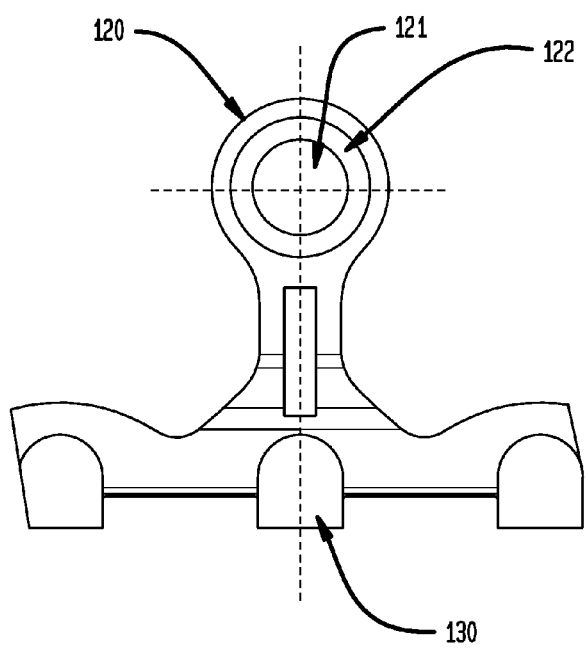
FIG. 2C is a partial frontal view of the first plate shown in FIG. 1.
Figure 2D:
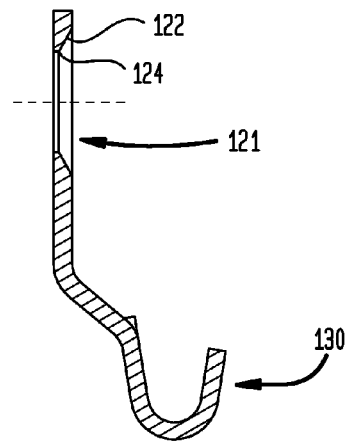
FIG. 2D is a cross-section of the first plate shown in FIG. 1 at an attachment loop.

Referring to the drawings, wherein like reference numerals refer to like elements, FIGS. 1-4C depict components usable in methods including, but not limited to, treatment of human maxillary and mandibular fractures, restoration and fixation of dental occlusion, and maxillary and/or mandibular reconstruction with or without bone grafts. At the outset, it is to be understood that while the various components discussed herein are directed toward a use in connection with fractured maxillary or mandible bones, such components may be modified (if necessary) to have applicability in the repair of fractures in other bones in human or animal bodies. Those of ordinary skill in the art would readily recognize that such components, although discussed in connection with a single purpose, have applicability for other purposes in the orthopedic field.

Beginning with FIG. 1, and according to one embodiment, a plate system 100 includes a plate 110 having a plurality of stems 140, a plurality of attachment loops 120 at the distal ends of the stems 140, and a plurality of hooks 130. Although the preferred embodiments depict a certain number of stems, loops and hooks it is to be understood that plates having any number of such components are contemplated and thusly clearly within the scope of the invention. In certain embodiments, one or more stem 140 may be rigid or bendable, and plate 110 may likewise be bendable so as to be capable of approximating the shape of a maxillary or mandibular arch, as shown in FIG. 1. Plate 110 may be constructed from a variety of materials suitable for implantation in the body, e.g., metals such as stainless steel or titanium and polymers such as PEEK.

As used herein, the terms "bendable" and "rigid" are to have a meanings as disclosed in the '850 patent. An element that is described as "bent" is equivalent to "bendable" for the purposes of this application.

In one embodiment, attachment loops 120 and hooks 130 may be a single material formed integral with the remainder of plate 110. In other embodiments, attachment loops 120 and hooks 130 may be made from separate material, as disclosed in the '850 patent. Attachment loops 120 provide a location at which plate 110 may be secured to a bone fragment such as a maxilla or a mandible using a bone screw or other fastener, but are not limited to such application. Attachment loops 120 are preferably evenly spaced along the length of the plate 110.

As shown in FIGS. 2A-2D, and as disclosed in U.S. Pat. No. 6,322,562 ("the '562 patent"), the disclosure of which is hereby incorporated by reference herein, attachment loops 120 include a circular opening 121, although, in other embodiments, the opening may be of any shape. The cross-sectional view of FIG. 2D further illustrates that attachment loop 120 includes a top countersunk 122 which decreases toward the bottom of the hole to form a lip 124, also disclosed in FIG. 2A of the '562 patent, with alternative embodiments as disclosed in FIGS. 2B-2I of the '562 patent. Lip 124 may be designed so as to allow for a rigid connection with a bone screw, like the bone screws discussed below. This may include lip 124 being formed of a material which is softer than a material of such bone screw. One such type of design is currently offered in various bone plates offered by Stryker Trauma GmbH under the tradenames, VARIAX® and SMARTLOCK®. In addition, the '562 patent discloses a similar screw fixation concept.

As noted above, insertion of bone screws into teeth or roots of teeth pathway should be avoided. Stems 140 are preferably positioned on plate 110 so that any screw placed through attachment loops 120 are positioned between roots 150 of the teeth (shown in phantom in FIG. 1). For any stem that does not align between the apparent root locations, the bendability of such stem may allow for the avoidance of root 150. This characteristic is illustrated in FIG. 1, where stem 140a is so adjusted. Adjustments of the stem 140 position may also be made as desired by the treating surgeon or other medical professional.

In one embodiment, hooks 130 are formed integral with the remainder of plate 110. This construction is shown more specifically in FIGS. 2A-2D. A securing wire 170 is shown in FIG. 1 in engagement with hooks 130 for the purpose of IMF. More particularly, IMF is accomplished through use of securing wire 170 attached to the plate 110 by placing securing wire around opposing hooks 130, i.e. connecting plate system 100 with plate system 200, and by twisting the ends of the wire around each other. This may involve connecting single hooks 130 on each side, or connections in greater multiples, such as over two hooks on the maxillary plate 110 and two hooks on the mandible plate 210. Greater fixation may be achieved through the placement of additional securing wires 170 around additional hooks 130. FIG. 1 illustrates an embodiment that uses securing wire for IMF, however, other suitable ligatures that are known to those of skill in the art may be used in the place of securing wire. Non-limiting examples of such alternatives include plastic loops or elastomeric members, such as elastic bands.

Figure 3A:
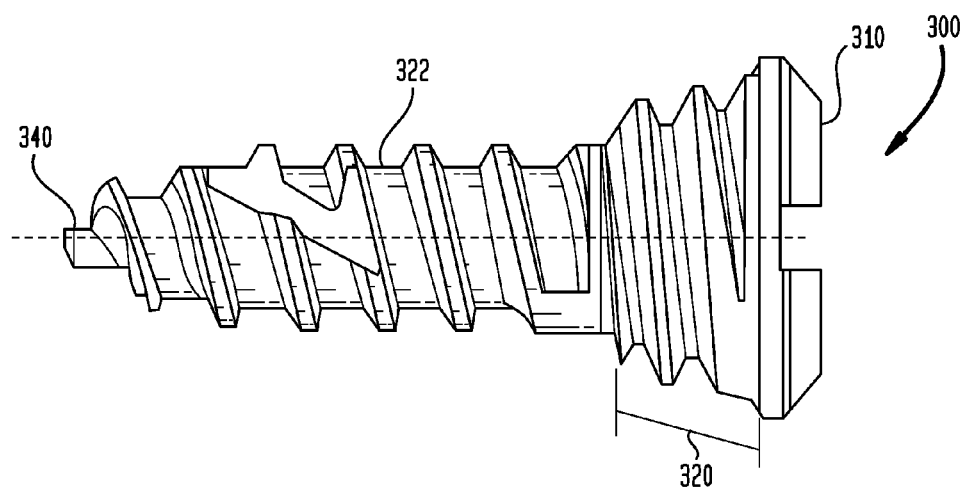
FIG. 3A is a frontal view of a bone screw shown in FIG. 1.
Figure 3B:
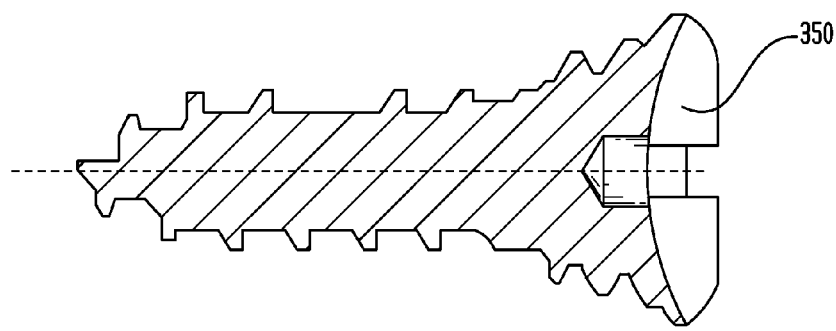
FIG. 3B is a cross section of the bone screw of FIG. 3A along the longitudinal axis.
Figure 3C:
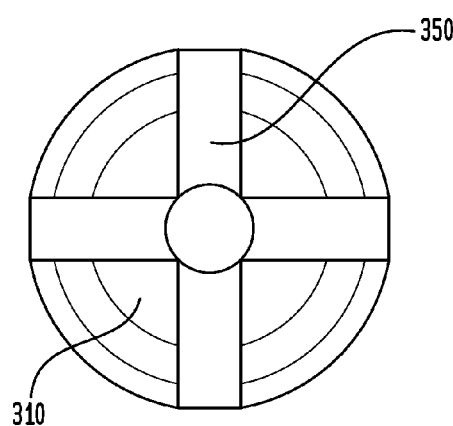
FIG. 3C is a top view of the bone screw of FIG. 3A.

Although a variety of fasteners may be used to attach the plate 110 to a maxilla, mandible, or other bone fragment, a particular embodiment is depicted in FIGS. 3A-3C. Bone screw 300 includes a screw head 310 having two recesses on perpendicular axes to form a cross-recess screw drive 350. Distal from the top of the screw head 310 and immediately thereunder is a countersunk preformed thread 320. The preformed thread 320 may function to engage with the lip 124, as discussed above. In this regard, thread 320 may be formed of a harder material than lip 124. Further thereunder there is a screw shank 322, which may be of a design known to those of skill in the art. However, in accordance with the present invention, it is preferable for shank 322 to be of a self-tapping design, e.g., by including tapping tip 340.

FIGS. 4A-4C depict a spacer for use in implanting plate 110 in accordance with the present invention. As shown, spacer 400 includes a shaft 410 having top surface 420a, a bottom surface 420b and side surfaces 430a, 430b. A distal end 404 of spacer 400 includes a curved portion having a fork 405 at a distal-most portion. A distal end 402 extends parallel to the body of the shaft 410 having a fork 403 at a distal-most portion. The forks 403, 405 include at least opposing tines 440a, 440b, but may include more than two such tines. As shown, tines 440a, 440b are symmetric about the longitudinal axis of the shaft 410 on the plane of top and bottom surfaces 420a, 420b, and each of tines 440a, 440b has an extent that curves laterally outward away from the centerline of shaft 410 to form a central pocket 450. In this manner, spacer 400 may be placed adjacent to bone and central pocket 450 may allow a fastener to be inserted therethrough. The placement of the spacer 400 also ensures that the plate 110 is elevated from the bone and/or gingiva after insertion of the bone screw 300.

In other embodiments, the distal ends 402, 404 may be curved, staggered, or designed to accommodate various shapes and configurations known to those of skill in the art. Combinations of distal end 402, 404 and fork 403, 405 designs, including the number and shape of tines, are not limited by the choice of either. Specific fork 403, 405 and distal end 402, 404 designs for a particular embodiment may be any known to those of skill in the art. Use of a particular combination may provide additional versatility for bone screw insertion but is not limited to this application.

In use, plate 110 may first be bent to approximate the bone on which it is to be implanted. As shown in the particular embodiment of FIG. 1, this includes approximating the plate to the dental arch of a patient. Spacer 400 may then be placed adjacent the bone over the desired location of fixation between the plate system and bone. Holding the spacer 400 in position, plate 110 may then be positioned as desired and bone screw 300 inserted through attachment loop 120. As discussed above, because of its design bone screw 300 forms a fixed connection to both plate 110 and the bone. Because of the placement of spacer 400 this results in plate 110 being elevated from the bone after insertion of screw 300. A similar process may be followed for the placement of subsequent screws in the plate.

More particularly, once the insertion point for the bone screw 300 has been established and the stem 140 of the plate 110 has been adjusted if required (i.e., for placement away from the roots 150 of teeth), a portion of spacer 400 is placed over the bone so that tines 440a, 440b are adjacent to the bone surface. Then, plate 110 and corresponding attachment loop 120 may be placed over the spacer 400 such that a space between plate 110 and the bone is created by the spacer 400. Bone screw 300 is then inserted into the attachment loop 120 of the plate 110 and between tines 440a, 440b (within pocket 450). Insertion of bone screw 300 allows for the countersunk preformed thread 320 feature to deform lip 124 of attachment loop 120 so that the screw becomes fixed to the plate. In this manner, because of the spacing between plate 110 and the bone, no pressure is created on the bone. The screw insertion procedure is then repeated at other desired locations.

Certain other steps may also be performed in accordance with the method of the present invention. For example, a cutter or other tool known to those of skill in the art may be used to cut plate 110 at one end in a direction transverse to the longitudinal axis of the plate 110 to approximate the length of a particular maxillary or mandible arch. This, in addition to the above-discussed bending, may allow for proper fitting to the subject bone. As discussed above, attachment loops 120 may also be bent to allow for their positioning between any roots 150 of adjacent teeth. In this manner, bone screw 300 may be inserted through a bent attachment loop 120 into a bone fragment between the roots 150 of teeth.

As shown in FIG. 1, the present invention may involve the implantation of two plates, above-described plate 110 and a similar plate 210. Although not specifically discussed in detail herein, plate 210 includes very similar components to that of plate 110, all described using the 200-series of numbers. Thus, for example, attachment loops 120 and 220 are of a similar or identical design. Of course, depending upon the particular uses for the plates, such may differ from one another. For instance, plate 210 may be specifically designed for implantation on the mandible.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of fixation comprising the steps of: placing a portion of a spacer adjacent a first bone at a first location; placing a first plate so that the portion of the spacer is between the first plate and the first bone, wherein the portion of the spacer placed adjacent to the first bone at the first location includes tines; inserting a first bone screw through the first plate at the first location while the portion of the spacer remains between the first plate and the first bone, wherein the first bone screw is inserted through the tines; and removing the portion of the spacer from between the first plate and the first bone so that the first plate remains spaced apart from the first bone.

2. The method of claim 1, wherein the first bone is a maxilla and the method further includes the step of bending the first plate to approximate the shape of the maxilla.

3. The method of claim 1, wherein the first bone is a mandible and the method further includes the step of bending the first plate to approximate the shape of the mandible.

4. The method of claim 1, wherein the tines having tapered distal ends.

5. The method of claim 1, wherein the first bone screw is inserted through a first attatchment loop of the first plate.

6. The method of claim 5, further comprising the step of bending the first attachment loop with respect to the remainder of the first plate.

7. The method of claim 1, further comprising the steps of placing the portion of the spacer adjacent the first bone at a second location and inserting a second bone screw through the first plate at the second location while the portion of the spacer remains between the first plate and the first bone.

8. The method of claim 7, wherein the portion of the spacer placed adjacent the first bone at the second location includes tines having tapered distal ends.

9. The method of claim 8, wherein the second bone screw is inserted through the tines.

10. The method of claim 9, wherein the second bone screw is inserted through a second attachment loop of the first plate.

11. The method of claim 10, further comprising the step of bending the second attachment loop with respect to the remainder of the first plate.

12. The method of claim 1, wherein the step of inserting the first bone screw includes fixing a portion of the first bone screw to the first plate.

13. The method of claim 12, wherein the first bone screw includes a first bone screw head formed of a hard material and the first plate includes a portion formed of a soft material and insertion of the first bone screw results in the first bone screw head deforming the portion of the first plate.

14. The method of claim 1, wherein the first bone is the maxilla and the method further comprises the steps of:
   placing a portion of the spacer adjacent to a second bone at a second location, the second bone being the mandible;
   placing a second plate so that the portion of the spacer is between the second plate and the second bone;
   inserting a second bone screw through the second plate at the second location while the portion of the spacer remains between the second plate and the second bone; and
   removing the portion of the spacer from between the second plate and the second bone so that the second plate remains spaced apart from the second bone.

15. A method of fixation comprising the steps of:
   placing a portion of a spacer adjacent a first bone at a first location;
   placing a first plate so that the portion of the spacer is between the first plate and the first bone, wherein the portion of the spacer placed adjacent to the first bone at the first location includes tines having tapered distal ends;
   inserting a first bone screw through the first plate at the first location while the portion of the spacer remains between the first plate and the first bone, wherein a portion of the first bone screw is fixed to the first plate; and
   removing the portion of the spacer from between the first plate and the first bone so that the first plate remains spaced apart from the first bone.

* * * * *